United States Patent
Roh et al.

(10) Patent No.: US 11,834,395 B2
(45) Date of Patent: Dec. 5, 2023

(54) METHOD FOR PREPARING HYDROGENATED BISPHENOL A

(71) Applicant: KOREA KUMHO PETROCHEMICAL CO., LTD., Seoul (KR)

(72) Inventors: Kee Yoon Roh, Daejeon (KR); Jung Hee Jang, Daejeon (KR); Je Young Park, Daejeon (KR); Nam Hyun Cho, Daejeon (KR)

(73) Assignee: KOREA KUMHO PETROCHEMICAL CO., LTD., Seoul (KR)

( * ) Notice: Subject to any disclaimer, the term of this patent is extended or adjusted under 35 U.S.C. 154(b) by 0 days.

(21) Appl. No.: 17/944,676

(22) Filed: Sep. 14, 2022

(65) Prior Publication Data
US 2023/0084194 A1 Mar. 16, 2023

(30) Foreign Application Priority Data
Sep. 15, 2021 (KR) .......... 10-2021-0122926

(51) Int. Cl.
*C07C 29/20* (2006.01)

(52) U.S. Cl.
CPC .......... *C07C 29/20* (2013.01); *C07C 2601/14* (2017.05)

(58) Field of Classification Search
CPC ...... C07C 29/20; C07C 2601/14; C07C 29/19
See application file for complete search history.

(56) References Cited

U.S. PATENT DOCUMENTS

| 4,885,409 | A | 12/1989 | Gardano et al. |
| 7,960,444 | B2 | 6/2011 | Lysenko et al. |
| 9,545,617 | B2 | 1/2017 | Wu et al. |
| 10,611,712 | B2 * | 4/2020 | Liao ........ B01J 23/462 |
| 2018/0346398 | A1 | 12/2018 | Liao et al. |

FOREIGN PATENT DOCUMENTS

| CN | 106083529 A | 11/2016 | |
| CN | 106866365 A | 6/2017 | |
| CN | 109678661 A | 4/2019 | |
| CN | 113045384 A | 6/2021 | |
| JP | 3-157342 A | 7/1991 | |
| JP | H069461 * | 1/1994 | ............. Y02P 20/52 |
| JP | 2000-44503 A | 2/2000 | |
| JP | 2003-2853 A | 1/2003 | |
| RU | 2005 136 653 A | 5/2006 | |
| TW | 201522293 A | 6/2015 | |
| WO | 2015/068677 A1 | 5/2015 | |

OTHER PUBLICATIONS

International Search Report dated Sep. 14, 2022 in Application No. PCT/KR2022/007088.
Tang et al., "Synthesis of jet fuel range high-density polycycloalkanes with polycarbonate waste", Green Chemistry, vol. 21, No. 14, pp. 3789-3795, 2019 (26 pages) pp. S1-S25.
Extended European Search Report dated Feb. 1, 2023 from the European Patent Office in EP Application No. 22191214.0.

* cited by examiner

*Primary Examiner* — Rosalynd A Keys
(74) *Attorney, Agent, or Firm* — Sughrue Mion, PLLC

(57) ABSTRACT

An embodiment of the present invention provides a method for preparing hydrogenated bisphenol A, comprising: (a) heating a reactor in which bisphenol A, a solvent, and a ruthenium supported catalyst are added; (b) supplying hydrogen into the reactor to react; and (c) blocking the supply of hydrogen to react.

6 Claims, No Drawings

METHOD FOR PREPARING HYDROGENATED BISPHENOL A

TECHNICAL FIELD

The present invention relates to a method for preparing hydrogenated bisphenol A.

BACKGROUND ART

Hydrogenated bisphenol A, i.e., 2,2-bis(4-hydroxycyclohexyl)propane, is a useful raw material for polymer polymerization. For example, a polyester resin prepared by polycondensing hydrogenated bisphenol A with a dibasic acid such as phthalic acid or maleic acid exhibits excellent heat resistance and moisture resistance. An epoxy resin prepared by reacting hydrogenated bisphenol A with epichlorohydrin has excellent electrical properties, exhibits less yellowing for not including an aromatic ring, and thus may be used in places requiring weather resistance, and has excellent operability at low viscosity. In addition, due to the controversy over the harmfulness of bisphenol A, international demand for environment-friendly products as a substitute for bisphenol A is on the increase.

In order to prepare hydrogenated bisphenol A, many researchers have been studying a method of adding hydrogen to the aromatic ring of bisphenol A using a metal supported catalyst. It has been mainly reported that the yield and/or reaction rate of hydrogenated bisphenol A may be improved by using an improved metal supported catalyst or by using a specific reaction solvent. However, the prior art still has problems in terms of economic feasibility considering the price of the catalyst, the reaction yield of hydrogenated bisphenol A, the reaction time, etc.

In general, hydrogenated bisphenol A prepared by hydrogenation of bisphenol A is a mixture of three types of stereoisomers, i.e., cis/cis isomer, cis/trans isomer, and trans/trans isomer, depending on the three-dimensional structure of the two cyclohexanes bridged by an isopropylidene group. Among the stereoisomers of hydrogenated bisphenol A, the trans/trans isomer is known to have the most stable structure. When using hydrogenated bisphenol A with a high ratio of trans/trans isomer, it becomes possible to polymerize a polymer resin with excellent performance such as hardness and glass transition temperature, etc. Accordingly, there is a request for developing a process for preparing hydrogenated bisphenol A with a high ratio of trans/trans isomer.

DETAILED DESCRIPTION OF INVENTION

Technical Task

The present invention aims at solving the problems of the prior art described above. It is an object of the present invention to provide a method for preparing hydrogenated bisphenol A with a high yield and a high trans/trans isomer ratio.

Means for Solving Technical Task

According to an aspect, a method for preparing hydrogenated bisphenol A, comprising: (a) heating a reactor in which bisphenol A, a solvent, and a ruthenium supported catalyst are added; (b) supplying hydrogen into the reactor to react; and (c) blocking the supply of hydrogen to react, is provided.

In an embodiment, in step (b), the hydrogen may be supplied at a pressure of 30 to 60 bar.

In an embodiment, step (b) may comprise: (b1) supplying hydrogen at a pressure of 30 to 45 bar into the reactor with an internal temperature of 90 to 120° C.; and (b2) supplying hydrogen at a pressure of 45 to 60 bar into the reactor with an internal temperature of 120 to 160° C.

In an embodiment, the reaction time in step (b) may be 30 to 180 minutes.

In an embodiment, the reaction temperature in each of step (b) and step (c) may be 120 to 160° C.

In an embodiment, the reaction pressure in each of steps (b) and (c) may be 30 to 60 bar.

In an embodiment, the reaction time in step (c) may be 30 to 90 minutes.

In an embodiment, the ratio of hydrogenated bisphenol A in the product of step (c) may be 96% or more.

In an embodiment, the ratio of trans/trans isomer of hydrogenated bisphenol A in the product of step (c) may be 45% or more.

Effect of Invention

According to an aspect of the present specification, hydrogenated bisphenol A with a high ratio of trans/trans isomer may be prepared in a high yield.

In addition, the method for preparing hydrogenated bisphenol A according to another aspect of the present specification has a short reaction time and allows the catalyst to be reused, and thus may be applied to an economic and environment-friendly process.

The effects of an aspect of the present invention are not limited to the above-mentioned effects, and it should be understood that the effects of the present invention include all effects that could be inferred from the configuration of the invention described in the detailed description of the invention or the appended claims.

BEST MODE FOR CARRYING OUT THE INVENTION

Hereinafter, an aspect of the present specification will be described. However, the description of the present specification may be implemented in various different forms, and thus is not limited to the embodiments described herein.

Throughout the specification, it will be understood that when a portion is referred to as being "connected" to another portion, it can be "directly connected to" the other portion, or "indirectly connected to" the other portion having intervening portions present. Also, when a component "includes" an element, unless there is another opposite description thereto, it should be understood that the component does not exclude another element but may further include another element.

When a range of numerical values is described herein, the value has the precision of the significant figures provided according to the standard rules in chemistry for significant figures, unless a specific range thereof is stated otherwise. For example, 10 includes a range of 5.0 to 14.9 and the number 10.0 includes a range of 9.50 to 10.49.

As used herein, the term "bisphenol A (BPA)" refers to 2,2-bis(4-hydroxyphenyl)propane.

As used herein, the term "hydrogenated bisphenol A (HBPA)" refers to 2,2-bis(4-hydroxycyclohexyl)propane.

The method for preparing hydrogenated bisphenol A according to an aspect of the present specification comprises: (a) heating a reactor in which bisphenol A, a solvent, and a ruthenium supported catalyst are added; (b) supplying hydrogen into the reactor to react; and (c) blocking the supply of hydrogen to react.

Step (a) is a step for adding bisphenol A, a solvent, and a ruthenium supported catalyst, which are the raw materials, to the reactor, and raising the temperature inside by heating the reactor to prepare for the reaction.

As the solvent, any kind of solvent capable of dissolving bisphenol A may be used. For example, the solvent may be an alcohol-type solvent selected from the group consisting of methanol, ethanol, propanol, isopropanol, and combinations of two or more thereof, but is not limited thereto.

When the ruthenium supported catalyst is applied to the preparation method, it may be reused in the process for preparing hydrogenated bisphenol A for 20 or more times without an additional input of the catalyst and delay of reaction time. Even when the catalyst is reused, the hydrogenated bisphenol A prepared by the method for preparing hydrogenated bisphenol A according to an embodiment of the present specification may maintain a high yield and a high ratio of trans/trans isomer of the hydrogenated bisphenol A in the product. Due to the high reusability of the catalyst, economic feasibility of the process may be improved, and an environment-friendly process may be designed.

The catalyst may be one in which ruthenium is supported in a carrier such as diatomaceous earth, pumice, activated carbon, silica gel, alumina, zirconium oxide, or titanium oxide. For example, the catalyst may be a Ru/C catalyst in which ruthenium is supported in a carbon-based support, but is not limited thereto.

The content of ruthenium in the catalyst may be 0.1 to 20% by weight based on the total weight of the catalyst. For example, the content of ruthenium may be 0.1% by weight, 1% by weight, 2% by weight, 3% by weight, 4% by weight, 5% by weight, 6% by weight, 7% by weight, 8% by weight, 9% by weight, 10% by weight, 11% by weight, 12% by weight, 13% by weight, 14% by weight, 15% by weight, 16% by weight, 17% by weight, 18% by weight, 19% by weight, 20% by weight, or a range between any two of these values.

The content of the catalyst may be 0.5 to 10 parts by weight based on 100 parts by weight of the bisphenol A. For example, the content of the catalyst may be 0.5 parts by weight, 1 part by weight, 2 parts by weight, 3 parts by weight, 4 parts by weight, 5 parts by weight, 6 parts by weight, 7 parts by weight, 8 parts by weight, 9 parts by weight, 10 parts by weight or a value between any two of these values, but is not limited thereto. When the content of the catalyst deviates from the above range, the reaction time may increase, thereby degrading the process efficiency, and lowering the ratio of trans/trans isomer of hydrogenated bisphenol A in the final product.

Step (b) is a step for performing hydrogenation reaction, i.e., hydrogen addition reaction, and in step (b), hydrogen is supplied to the reactor to react so that hydrogen is added to the aromatic ring of bisphenol A which is the raw material.

In step (b), the hydrogen may be supplied at a pressure of 30 to 60 bar. For example, the pressure may be 30 bar, 32 bar, 34 bar, 36 bar, 38 bar, 40 bar, 42 bar, 44 bar, 46 bar, 48 bar, 50 bar, 52 bar, 54 bar, 56 bar, 58 bar, 60 bar or a range between any two of these values. When the hydrogen supply pressure deviates from the above range, the yield of hydrogenated bisphenol A may deteriorate.

Step (b) may comprise: (b1) supplying hydrogen at a pressure of 30 to 45 bar in a reactor with an internal temperature of 90 to 120° C.; and (b2) supplying hydrogen at a pressure of 45 to 60 bar in a reactor with an internal temperature of 120 to 160° C. The yield of hydrogenated bisphenol A may be improved by adjusting the hydrogen supply pressure according to the temperature change inside the reactor.

The reaction time in step (b) may be 30 to 180 minutes. For example, the reaction time may be 30 minutes, 40 minutes, 50 minutes, 60 minutes, 70 minutes, 80 minutes, 90 minutes, 100 minutes, 110 minutes, 120 minutes, 130 minutes, 140 minutes, 150 minutes, 160 minutes, 170 minutes, 180 minutes or a range between any two of these values. When the reaction time is shorter than the above range, the hydrogenation reaction may not proceed sufficiently, and thus the yield of hydrogenated bisphenol A may rapidly deteriorate. When the reaction time is longer than the above range, process efficiency and economic feasibility may deteriorate.

Step (c) is a step for obtaining a product by performing an additional reaction after blocking the hydrogen supply in step (b). By blocking the hydrogen supply and performing an additional reaction, the ratio of trans/trans isomer of the hydrogenated bisphenol A in the product may be improved.

The reaction temperature in each of steps (b) and (c) may be 120 to 160° C. For example, the reaction temperature may be 120° C., 125° C., 130° C., 135° C., 140° C., 145° C., 150° C., 155° C., 160° C., or a range between any two of these values. When the reaction temperature is lower than the above range, the yield of hydrogenated bisphenol A and the ratio of trans/trans isomer of the hydrogenated bisphenol A in the product may deteriorate. When the reaction temperature is higher than the above range, the yield of hydrogenated bisphenol A may decrease and the production of impurities may increase.

The reaction temperature in step (b) and the reaction temperature in step (c) may be the same or different.

The reaction pressure in each of steps (b) and (c) may be 30 to 60 bar. For example, the reaction pressure may be 30 bar, 32 bar, 34 bar, 36 bar, 38 bar, 40 bar, 42 bar, 44 bar, 46 bar, 48 bar, 50 bar, 52 bar, 54 bar, 56 bar, 58 bar, 60 bar or a range between any two of these values. The reaction pressure in step (b) and the reaction pressure in step (c) may be the same or different.

The reaction time in step (c) may be 30 to 90 minutes. For example, the reaction time may be 30 minutes, 40 minutes, 50 minutes, 60 minutes, 70 minutes, 80 minutes, 90 minutes, or a range between any two of these values. When the reaction time in step (c) is shorter than the above range, the yield of hydrogenated bisphenol A and the ratio of trans/trans isomer of the hydrogenated bisphenol A in the product may deteriorate. When the reaction time is longer than the above range, process efficiency and economic feasibility may deteriorate.

The total reaction time in steps (b) and (c) may be 90 to 240 minutes. For example, the total reaction time may be 90 minutes, 100 minutes, 110 minutes, 120 minutes, 130 minutes, 140 minutes, 150 minutes, 160 minutes, 170 minutes, 180 minutes, 190 minutes, 200 minutes, 210 minutes, 220 minutes, 230 minutes, 240 minutes or a range between any two of these values. The method for preparing hydrogenated bisphenol A according to an embodiment of the present specification has a shorter reaction time than the prior art, and thus may improve process efficiency.

The method for preparing hydrogenated bisphenol A according to an embodiment of the present specification may improve the yield of hydrogenated bisphenol A and the ratio of trans/trans isomer of hydrogenated bisphenol A in the product by performing an additional reaction after blocking hydrogen supply, and may improve process efficiency and economic feasibility by reducing reaction time as compared to prior art.

The ratio of hydrogenated bisphenol A in the product of step (c) may be 96% or more. For example, the ratio may be 96% or more, 96.5% or more, 97% or more, 97.5% or more, 98% or more, 98.5% or more, 99% or more, or 99.5% or more.

The hydrogenated bisphenol A in the product of step (c) may be a mixture of cis/cis isomer, cis/trans isomer, and trans/trans isomer, and the content of trans/trans isomer may be the highest among the three types of isomers.

The ratio of trans/trans isomer of hydrogenated bisphenol A in the product of step (c) may be 45% or more. For example, the ratio may be 45% or more, 46% or more, 47% or more, 48% or more, 49% or more, 50% or more, 51% or more, 52% or more, 53% or more, 54% or more, or 55% or more. The hydrogenated bisphenol A prepared according to the method for preparing hydrogenated bisphenol A according to an embodiment of the present specification has a high ratio of trans/trans isomer, and thus when applied to a polymer resin polymerization process, performance such as hardness and glass transition temperature of the polymer resin may be improved.

The ratio of hydrogenated bisphenol A intermediate in the product of step (c) may be 1.0% or less. For example, the ratio may be 1.0% or less, 0.9% or less, 0.8% or less, 0.7% or less, 0.6% or less, 0.5% or less, 0.4% or less, 0.3% or less, 0.2% or less, or 0.1% or less.

The method for preparing hydrogenated bisphenol A may further comprise: (d) purifying the product of step (c) to obtain hydrogenated bisphenol A.

Step (d) may be performed through a distillation process after lowering the temperature of the reactor in which the reaction is completed. The purity of hydrogenated bisphenol A after the purification in step (d) may be 97% or more. For example, the purity may be 97% or more, 97.5% or more, 98% or more, 98.5% or more, 99% or more, or 99.5% or more.

Hereinafter, embodiments of the present specification will be described in more detail. However, the following experimental results describe only representative experimental results among the above examples, and the scope and content of the present specification may not be construed as narrowed or limited by the examples. Each effect of the various embodiments of the present specification not explicitly presented below will be specifically described in the corresponding section.

EXAMPLE 1

After transferring 500 g of bisphenol A (BPA), 1,000 g of isopropanol (IPA) and 15 g of a 5% Ru/C catalyst to a hydrogenation reactor, nitrogen was substituted three times in the hydrogenation reactor at an internal pressure of 4 bar. The internal temperature was raised by supplying a heat source with steam while stirring the hydrogenation reactor. When the internal temperature of the reactor reached 100° C., hydrogen was added at an internal pressure of 40 bar, and when the internal temperature of the reactor reached 150° C., hydrogen was supplied at an internal pressure of 52 bar. Hydrogenation was performed for 60 minutes while maintaining the reaction temperature at 150±2° C., and then the hydrogen supply was blocked. After an additional reaction for at least 40 minutes at a reaction temperature of 150° C. and a reaction pressure of 50 bar under hydrogen blocking, the product was sampled at 10-minute intervals using a sampling port of the hydrogenation reactor to perform gas chromatography (GC) analysis. As a result of gas chromatography analysis, when the content of trans/trans isomer of the hydrogenated bisphenol A (HBPA) is 52% or more and the content of hydrogenated bisphenol A intermediate is 0.5% or less, the reaction was terminated, and the internal temperature of the reactor was lowered to 100° C. Then, the by-product was separated through a distillation process to obtain hydrogenated bisphenol A.

The gas chromatography analysis results over additional reaction time under hydrogen blocking are summarized in Table 1 below.

TABLE 1

| Reaction time (min) | Impurity (%) | HBPA yield (%) | HBPA isomer (%) | | | Others (%) |
|---|---|---|---|---|---|---|
| | | | cis/cis | cis/trans | trans/trans | |
| 40 | 2.36 | 97.05 | 9.86 | 41.93 | 45.26 | 0.59 |
| 50 | 2.35 | 97.06 | 7.25 | 39.25 | 49.32 | 0.59 |
| 60 | 2.34 | 97.06 | 6.54 | 37.97 | 51.58 | 0.6 |
| 70 | 2.33 | 97.08 | 5.74 | 36.46 | 54.88 | 0.07 |

Referring to Table 1, it may be confirmed that the yield of hydrogenated bisphenol A and the content of trans/trans isomer of the hydrogenated bisphenol A increased as the additional reaction time under hydrogen blocking increased. In particular, the content of the trans/trans isomer compared to the yield of hydrogenated bisphenol A sharply increased as the reaction time increased. As a result, in the case of a product subjected to an additional reaction for 70 minutes, the yield of hydrogenated bisphenol A was the highest, 97.08%, and at time same time, the content of trans/trans isomer of the hydrogenated bisphenol A was also the highest, 54.88%.

EXAMPLE 2

After transferring 500 g of bisphenol A (BPA), 1,000 g of isopropanol (IPA) and 15 g of a 5% Ru/C catalyst to a hydrogenation reactor, nitrogen was substituted three times in the hydrogenation reactor at an internal pressure of 4 bar. The internal temperature was raised by supplying a heat source with steam while stirring the hydrogenation reactor. When the internal temperature of the reactor reached 100° C., hydrogen was added at an internal pressure of 40 bar, and when the internal temperature of the reactor reached 140° C., hydrogen was supplied at an internal pressure of 52 bar. Hydrogenation was performed for 60 minutes while maintaining the reaction temperature at 140±2° C., and then the hydrogen supply was blocked. An additional reaction was performed for 70 minutes at a reaction temperature of 140° C. and a reaction pressure of 50 bar under hydrogen blocking. After performing gas chromatography analysis on the sampled product using a sampling port of the hydrogenation reactor, the reaction was terminated and the internal temperature of the reactor was lowered to 100° C. Then, the by-product was separated through a distillation process to obtain hydrogenated bisphenol A.

EXAMPLE 3

After transferring 500 g of bisphenol A (BPA), 1,000 g of isopropanol (IPA) and 15 g of a 5% Ru/C catalyst to a hydrogenation reactor, nitrogen was substituted three times in the hydrogenation reactor at an internal pressure of 4 bar.

The internal temperature was raised by supplying a heat source with steam while stirring the hydrogenation reactor. When the internal temperature of the reactor reached 100° C., hydrogen was added at an internal pressure of 40 bar, and when the internal temperature of the reactor reached 130° C., hydrogen was supplied at an internal pressure of 52 bar. Hydrogenation was performed for 60 minutes while maintaining the reaction temperature at 130±2° C., and then the hydrogen supply was blocked. An additional reaction was performed for 70 minutes at a reaction temperature of 130° C. and a reaction pressure of 50 bar under hydrogen blocking. After performing gas chromatography analysis on the sampled product using a sampling port of the hydrogenation reactor, the reaction was terminated and the internal temperature of the reactor was lowered to 100° C. Then, the by-product was separated through a distillation process to obtain hydrogenated bisphenol A.

In Examples 1 to 3, the gas chromatography analysis results of the products obtained after an additional reaction for 70 minutes are summarized in Table 2 below.

TABLE 2

| | Reaction temperature (° C.) | Impurity (%) | HBPA (%) yield | HBPA isomer (%) | | | |
|---|---|---|---|---|---|---|---|
| | | | | cis/cis | cis/trans | trans/trans | others (%) |
| Example 1 | 150 | 2.33 | 97.08 | 5.74 | 36.46 | 54.88 | 0.59 |
| Example 2 | 140 | 2.12 | 97.42 | 5.85 | 37.59 | 53.98 | 0.46 |
| Example 3 | 130 | 2.24 | 96.89 | 7.9 | 40.77 | 48.22 | 0.87 |

Referring to Table 2, the content of trans/trans isomer of the hydrogenated bisphenol A increased as the reaction temperature increased. Accordingly, the ratio of trans/trans isomer of the hydrogenated bisphenol A in the product of Example 1, which was reacted at 150° C., was the highest, 54.88%.

EXPERIMENTAL EXAMPLE

In order to evaluate the reusability of the 5% Ru/C catalyst used in Examples 1 to 3, a process for preparing hydrogenated bisphenol A was repeated 20 times in the same manner as in Example 1 without adding an additional catalyst.

As a result, the 20-time average yield of hydrogenated bisphenol A was 96.61%, and the 20-time average content of trans/trans isomer of hydrogenated bisphenol A was 52.5%.

That is, both the yield of hydrogenated bisphenol A and the content of trans/trans isomer of hydrogenated bisphenol A were kept constant. This confirms that the catalyst has excellent reusability and there was no delay in the reaction time.

The foregoing description of the present invention has been presented for illustrative purposes, and it is apparent to a person having ordinary skill in the art that the present invention can be easily modified into other detailed forms without changing the technical idea or the essential features of the present invention. Therefore, it should be understood that the forgoing embodiments are by way of example only, and are not intended to limit the present disclosure. For example, each component which has been described as a unitary part can be implemented as distributed parts. Likewise, each component which has been described as distributed parts can also be implemented as a combined part.

The scope of the present invention is presented by the accompanying claims, and it should be understood that all changes or modifications derived from the definitions and the scopes of the claims and their equivalents fall within the scope of the present invention.

What is claimed is:

1. A method for preparing hydrogenated bisphenol A, comprising:
   (a) heating a reactor in which bisphenol A, a solvent, and a ruthenium supported catalyst are added;
   (b) supplying hydrogen into the reactor to react; and
   (c) blocking the supply of hydrogen to react,
   wherein the reaction temperature in each of steps (b) and (c) is 140 to 160° C.,
   the reaction time in step (c) is 60 to 90 minutes, and
   a ratio of trans/trans isomer of hydrogenated bisphenol A in a product of step (c) is 51.58% or more.

2. The method of claim 1, wherein in step (b), the hydrogen is supplied at a pressure of 30 to 60 bar.

3. The method of claim 1, wherein step (b) comprises:
   (b1) supplying hydrogen at a pressure of 30 to 45 bar into the reactor with an internal temperature of 90 to 120° C.; and
   (b2) supplying hydrogen at a pressure of 45 to 60 bar into the reactor with an internal temperature of 120 to 160° C.

4. The method of claim 1, wherein the reaction time in step (b) is 30 to 180 minutes.

5. The method of claim 1, wherein the reaction pressure in each of steps (b) and (c) is 30 to 60 bar.

6. The method of claim 1, wherein the ratio of hydrogenated bisphenol A in the product of step (c) is 96% or more.

* * * * *